US010072260B2

(12) United States Patent
Happe et al.

(10) Patent No.: US 10,072,260 B2
(45) Date of Patent: Sep. 11, 2018

(54) TARGET ENRICHMENT OF RANDOMLY SHEARED GENOMIC DNA FRAGMENTS

(71) Applicant: Agilent Technologies, Inc., Loveland, CO (US)

(72) Inventors: Scott Robert Happe, Austin, TX (US); Emily Marine Leproust, San Jose, CA (US); Julia Barboza, Austin, TX (US); Joseph Hoang Hai Ong, Austin, TX (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 512 days.

(21) Appl. No.: 14/649,494

(22) PCT Filed: Oct. 3, 2013

(86) PCT No.: PCT/US2013/063290
§ 371 (c)(1),
(2) Date: Jun. 3, 2015

(87) PCT Pub. No.: WO2014/088694
PCT Pub. Date: Jun. 12, 2014

(65) Prior Publication Data
US 2015/0307875 A1      Oct. 29, 2015

Related U.S. Application Data

(60) Provisional application No. 61/734,251, filed on Dec. 6, 2012.

(51) Int. Cl.
*C12P 19/34* (2006.01)
*C12N 15/10* (2006.01)
*C12Q 1/6806* (2018.01)

(52) U.S. Cl.
CPC ....... *C12N 15/1068* (2013.01); *C12Q 1/6806* (2013.01)

(58) Field of Classification Search
None
See application file for complete search history.

(56) References Cited

U.S. PATENT DOCUMENTS

2008/0199916 A1    8/2008  Zheng et al.
2008/0242560 A1*  10/2008  Gunderson .......... B01J 19/0046
                                                                506/26

(Continued)

FOREIGN PATENT DOCUMENTS

CN          102344961 A      2/2012
CN      CN102344961 A1       2/2012

(Continued)

OTHER PUBLICATIONS

Callow, et al. "Selective DNA amplification from complex genomes using universal double-sided adapters" Nucleic Acids Research, 2004, 32(2): e21.

(Continued)

*Primary Examiner* — Kenneth R Horlick

(57) ABSTRACT

Provided herein are various methods for enriching a target fragment that is present in randomly sheared genomic DNA. In some embodiments, the method may involve hybridizing randomly sheared genomic DNA to a halo probe to produce a first circular complex, and then enzymatically digesting the overhanging ends of the genomic fragment. Other embodiments may include hybridizing randomly sheared genomic DNA to an RNA oligonucleotide that comprises a region that hybridizes to a fragment of the randomly sheared genomic DNA to produce an RNA/DNA duplex. The overhanging ends of the genomic fragment in the RNA/DNA duplex can then be enzymatically digested.

12 Claims, 4 Drawing Sheets

(56) References Cited

U.S. PATENT DOCUMENTS

2009/0156412 A1  6/2009  Boyce, IV et al.
2012/0003657 A1  1/2012  Myllykangas et al.

FOREIGN PATENT DOCUMENTS

JP    2007020474 A      2/2007
WO    WO2005/111236 A1  11/2005
WO    WO2005111236      11/2005

OTHER PUBLICATIONS

Callow, et al. "Selective DNA ampli®cation from complex genomes using universal double-sided adapters", Nucleic Acids Research, 2004, vol. 32, No. 2 e21.

* cited by examiner

TARGET ENRICHMENT OF RANDOMLY SHEARED GENOMIC DNA FRAGMENTS

BACKGROUND

Several analytical methods in molecular biology (e.g., sequencing library preparation) require that adaptor sequence by placed onto the end of an enriched DNA fragment in order to provide a way to manipulate that fragment. For example, one or more adaptors may be ligated onto an enriched fragment of DNA to produce an adaptor-ligated fragment, and the adaptor-ligated fragment may be amplified and/or sequenced using a primer binding site that are present in the added adaptor.

SUMMARY

Provided herein are various methods for enriching a target fragment that is present in randomly sheared genomic DNA. In some embodiments, the method may involve hybridizing randomly sheared genomic DNA to a halo probe to produce a first circular complex, and then enzymatically digesting the overhanging ends of the genomic fragment. Other embodiments may include hybridizing randomly sheared genomic DNA to an RNA oligonucleotide that comprises a region that hybridizes to a fragment of the randomly sheared genomic DNA to produce an RNA/DNA duplex. The overhanging ends of the genomic fragment in the RNA/DNA duplex can then be enzymatically digested. The resulting digested genomic fragment, which has defined ends, can be ligated to one or more oligonucleotides of the halo probe. The digested genomic fragment can then be amplified and sequenced.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
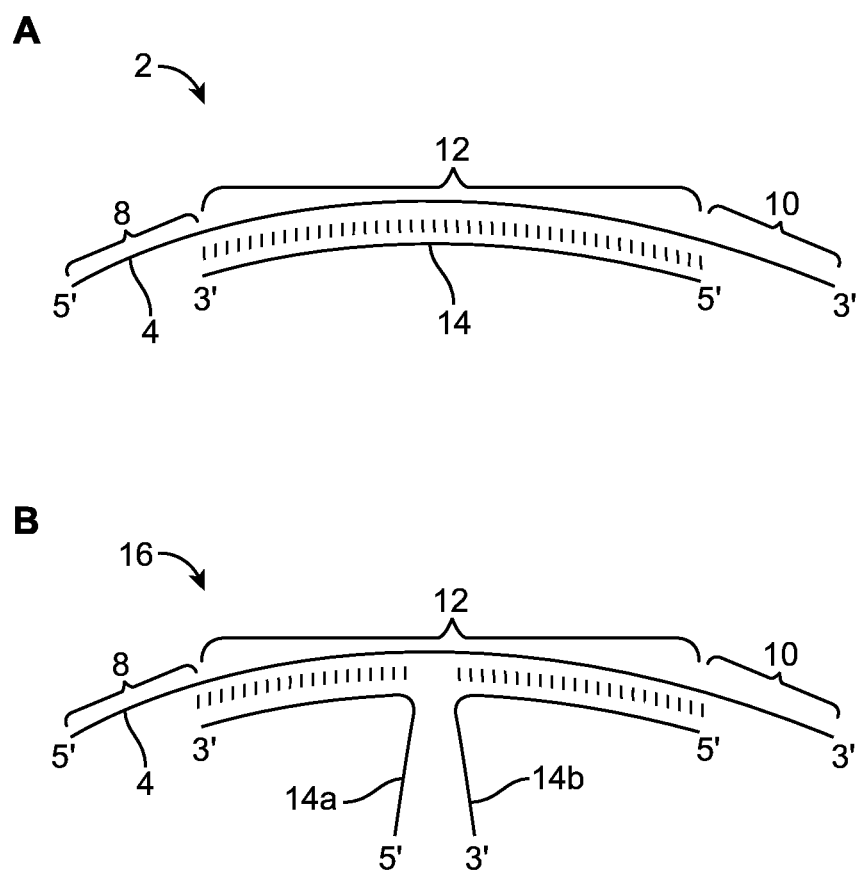
FIG. 1 schematically illustrates two embodiments of a halo probe.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest.

In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" also refers to "a biological sample." As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "A biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "biological sample" can also refer to cells or tissue analyzed in vivo, i.e., without removal from animal. Typically, a "biological sample" will contain cells from the animal, but the term can also refer to non-cellular biological material, such as non-cellular fractions of blood, saliva, or urine, that can be used to measure the cancer-associated polynucleotide or polypeptides levels. "A biological sample" further refers to a medium, such as a nutrient broth or gel in which an organism has been propagated, which contains cellular components, such as proteins or nucleic acid molecules.

The term "nucleic acid sample," as used herein denotes a sample containing nucleic acids. A nucleic acid samples used herein may be complex in that they contain multiple different molecules that contain sequences. Genomic DNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "target polynucleotide," as use herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5× Denhardt's solution, 0.5% SDS and 100 ug/ml denatured carrier DNA followed by washing two times in 2× SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "partitioning", with respect to a genome, refers to the separation of one part of the genome from the remainder of the genome to produce a product that is isolated from the remainder of the genome. The term "partitioning" encompasses enriching.

The term "genomic region", as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "genomic sequence", as used herein, refers to a sequence that occurs in a genome.

The term "genomic fragment", as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adaptor ligated (in which case it has an adaptor ligated to one or both ends of the fragment), or non-adaptor ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "affinity tag", as used herein, refers to moiety that can be used to separate a molecule to which the affinity tag is attached from other molecules that do not contain the affinity tag. An "affinity tag" is a member of a specific binding pair, i.e. two molecules where one of the molecules through chemical or physical means specifically binds to the other molecule. The complementary member of the specific binding pair, referred to herein as a "capture agent" may be immobilized (e.g., to a chromatography support, a bead or a planar surface) to produce an affinity chromatography support that specifically binds the affinity tag. In other words, an "affinity tag" may bind to a "capture agent", where the affinity tag specifically binds to the capture agent, thereby facilitating the separation of the molecule to which the affinity tag is attached from other molecules that do not contain the affinity tag.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

The term "terminal nucleotide", as used herein, refers to the nucleotide at either the 5' or the 3' end of a nucleic acid molecule. The nucleic acid molecule may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "digesting" is intended to indicate a process by which a nucleic acid is cleaved by enzyme such as an exonuclease or endonuclease, e.g., a restriction enzyme. In order to digest a nucleic acid, anenzyme and a nucleic acid are contacted under conditions suitable for the restriction enzyme to work. Conditions suitable for activity of commercially available restriction enzymes are known, and supplied with those enzymes upon purchase.

A "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "separating", as used herein, refers to physical separation of two elements (e.g., by size or affinity, etc.) as well as degradation of one element, leaving the other intact.

The term "target sequence" refers to a sequence that is in an unmodified genome, as well as genomes that have been modified (e.g., fragmented and/or adaptor-ligated) or copied. An oligonucleotide that hybridizes to a target genomic sequence base-pairs with the genome sequence. A genomic fragment that contains a target sequence may be in the range of 0.5 kb in length to over 500 kb in length or more, e.g., 5 kb to 100 kb, for example.

The term "reference chromosomal region," as used herein refers to a chromosomal region of known nucleotide sequence, e.g. a chromosomal region whose sequence is deposited at NCBI's Genbank database or other database, for example.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

As used herein, the term "label" refers to any atom or molecule that can be used to provide a detectable (preferably quantifiable) effect, and that can be attached to a nucleic acid or protein. Labels include but are not limited to dyes and radiolabels such as $^{32}P$; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable. The term "labeled dNTPs" refers to the dNTPs that are modified by the attached labels. The term "labeled ddNTPs" refers to the ddNTPs that are modified by the attached labels.

The term "labeled oligonucleotide", as used herein, refers to an oligonucleotide that is has an affinity tag (e.g., a biotin moiety) an oligonucleotide modified with atoms or groups enabling separation or detection (e.g., bromo-deoxyuridine, or colloidal gold particles conferring different density), an oligonucleotide modified with or an optically detectable label (e.g., a fluorescence or another type of light emitting label). Oligonucleotides that contain only naturally occurring nucleotides are not labeled oligonucleotides.

The term "adaptor" refers to double stranded adaptors, single stranded adaptors, and adaptors that are partially double stranded and partially single stranded. An adaptor can be DNA or RNA, or can contain both DNA and RNA.

The term "surface-tethered" refers to a molecule that is immobilized on a surface of a solid substrate, where the substrate can have a variety of configurations, e.g., a sheet, bead, or other structure.

The term "genotyping", as used herein, refers to any type of analysis of a nucleic acid sequence, and includes sequencing, polymorphism (SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "enzymatic processing" refers to a covalent modification that is catalyzed by an enzyme (e.g., a polymerase or restriction enzyme, for example). Primer extension (including PCR, rolling circle amplification), transcribing (e.g., using, e.g., T7 or T3 polymerase) and digesting (e.g., using a restriction enzyme) are all types of enzymatic processing).

The term "extending", as used herein, refers to the extension of a primer by the addition of nucleotides using a polymerase. If a primer that is annealed to a nucleic acid is extended, the nucleic acid acts as a template for extension reaction.

The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of a oligonucleotide. Barcode sequences may vary widely in size and composition; the following references provide guidance for selecting sets of barcode sequences appropriate for particular embodiments: Brenner, U.S. Pat. No. 5,635, 400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

As used herein, the term "flap cleavage reaction" refers to a reaction in which a substrate is cleaved in an overlap-dependent manner by a flap endonuclease to release a flap. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447).

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable.

Other definitions of terms may appear throughout the specification.

DESCRIPTION OF EXEMPLARY EMBODIMENTS

This disclosure provides a method for adding an adaptor to a genomic sequence by invasive cleavage, as well as a kit for performing the method. In certain embodiments, the method may be used to produce a library of randomly generated genomic fragments that each contain the adaptor sequence ligated thereto. These embodiments have particular application in whole genome sequencing. In other embodiments, the method may be used to produce a library of target genomic fragments that each contain the adaptor sequence ligated thereto. These embodiments have particular application in targeted re-sequencing applications and mapping of SNPs, for example.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

For reference purposes, two embodiments of a halo probe, 2 and 16 are shown in FIG. 1. As illustrated in FIG. 1, both embodiments of halo probe 2 and 16 comprise: (i) a first oligonucleotide 4 comprising flanking sequences 8 and 10 that hybridize to different regions in a fragment target DNA and a central sequence 12; and (ii) one or more second oligonucleotides that are complementary to the central sequence of the first oligonucleotide. In embodiment 2 (shown in panel A) the one or more second oligonucleotides can be a single oligonucleotide 14. In embodiment 16 (shown in panel B) the one or more second oligonucleotides can be two oligonucleotides 14a and 14b, which each contain a region that hybridizes to the first oligonucleotide, and a tail that does not hybridize to the first oligonucleotide. In certain embodiments, the one or more second oligonucleotides can provide amplification and/or sequencing primer binding sites, and, in addition a molecular barcode sequence. These sequences may be present in the tails of oligonucleotides 14a and 14b if halo probe 16 is used. Either of the halo probes shown in FIG. 1 may be used in the methods described below. Solely for convenience in explaining the method, the figures illustrate methods that use the first embodiment of a halo probe shown in panel A of FIG. 1.

Figure 2:
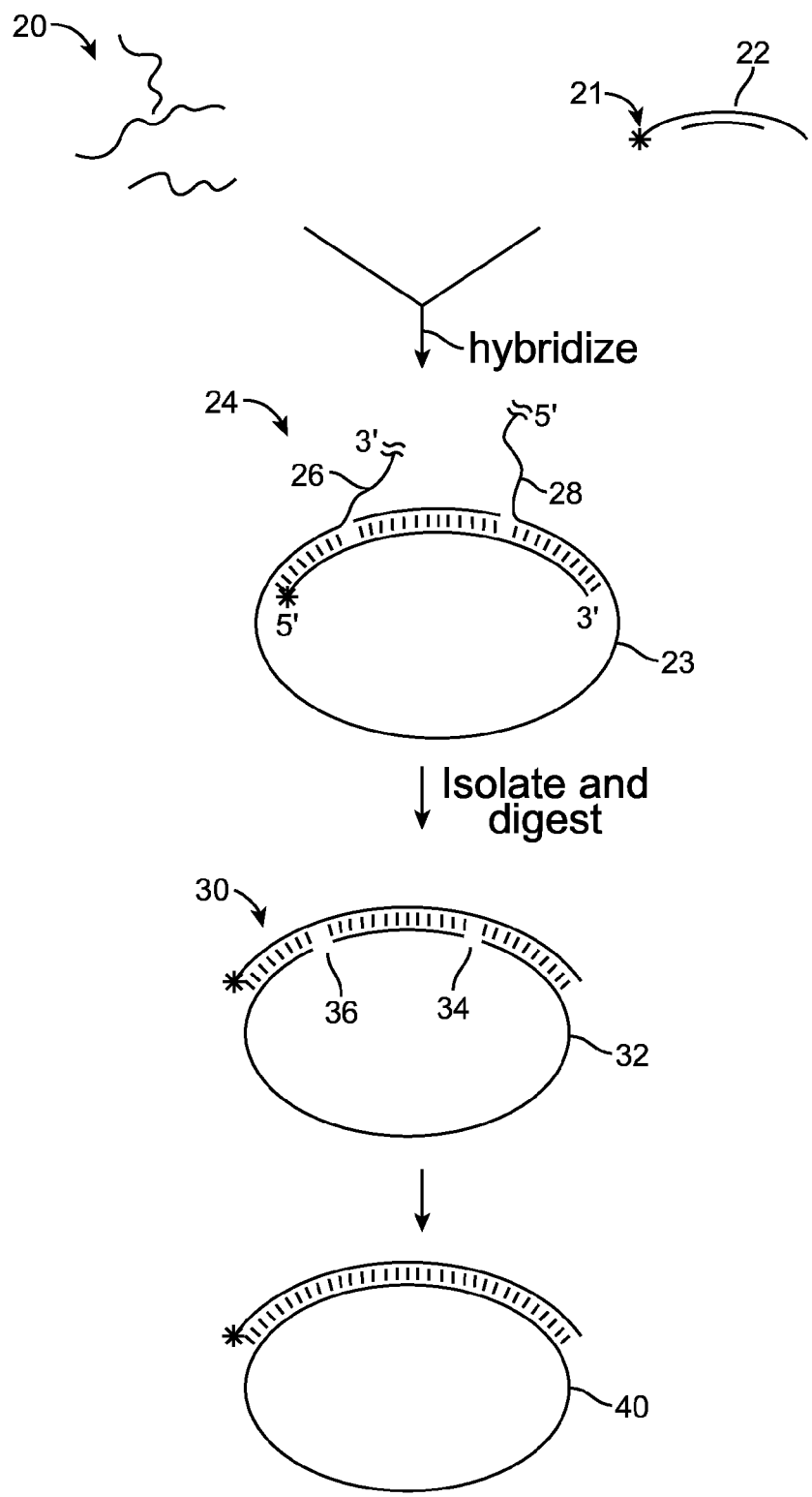
FIG. 2 schematically illustrates one embodiment of the method.

With reference to FIG. 2, one embodiment of the method comprises hybridizing randomly sheared genomic DNA 20 to halo probe 22 to produce a first circular complex 24. As noted above, the halo probe comprises: (i) a first oligonucleotide comprising flanking sequences that hybridize to different regions in a fragment of the randomly sheared genomic DNA and a central sequence; and (ii) one or more second oligonucleotides that are complementary to the central sequence of the first oligonucleotide. As illustrated, the first circular complex 24 comprises a fragment of the randomly sheared genomic DNA 23 that has overhang ends 26 and 28. As illustrated, the first oligonucleotide of the halo probe may contain an optional capture moiety 21, e.g., a biotin moiety, that can be used to isolate one of the complexes during the method. In these embodiments, the method may optionally involve isolating the first circular complex using the capture moiety prior to digestion. The next step of the method involves enzymatically digesting the overhanging ends of the genomic fragment in the first circular complex to provide a second circular complex 30 in which the 5' and 3' ends of the one or more second oligonucleotide are ligatably adjacent to the 3' and 5' ends of the digested genomic fragment 32. The enzymatically digesting may be done in a variety of different ways. For example, the enzymatically digesting may comprise digesting the first circular complex using a single-strand specific bi-directional exonuclease, exonuclease VII, in the option presence of a polymerase to fill in any ends that have been excessively digested. In other embodiments, the enzymatically digesting may comprises treatment with a cocktail comprising Pfu DNA polymerase and Taq DNA polymerase, a cocktail comprising T4 DNA polymerase and exonuclease VII, treatment with a mung bean nuclease, or treatment with a flap endonuclease in combination with a 3' exonuclease (e.g. exonuclease I, exonuclease T, exonuclease V), or sequential treatment with 5' and 3' exonucleases, for example. As shown in FIG. 2, this embodiment of the method comprises ligating the ligatable ends of the digested genomic fragment 32 to the ends of the one or more second oligonucleotides (i.e., ligating the ligatable junction 34 that is between the 3' end of the digested genomic fragment and the 5' end of the second oligonucleotide and ligating the ligatable junction 36 between the 5' end of the digested genomic fragment and the 3' end of the second oligonucleotide) to produce a circular DNA molecule 40. In certain embodiments (and as shown in FIG. 2) the circular DNA molecule 40 may be covalently circular in that the ends of the digested genomic fragment 32 are ligated to both ends of a single second oligonucleotide. In other embodiments, the circular DNA molecule 40 may be non-covalently circular if the second embodiment of the halo probe (shown in panel B of FIG. 1) is used. In these embodiments, the first oligonucleotide is hybridized to both the 5' end and the 3' end of the fragmented genomic fragment and holds ends of the fragment together to provide the circular DNA molecule. In these embodiments, the 5' end the digested genomic fragment 32 is ligated to the 3' end of one of the second oligonucleotides, and the 3' end the digested genomic fragment 32 is ligated to the 5' and of the other of the second oligonucleotides.

Figure 3:
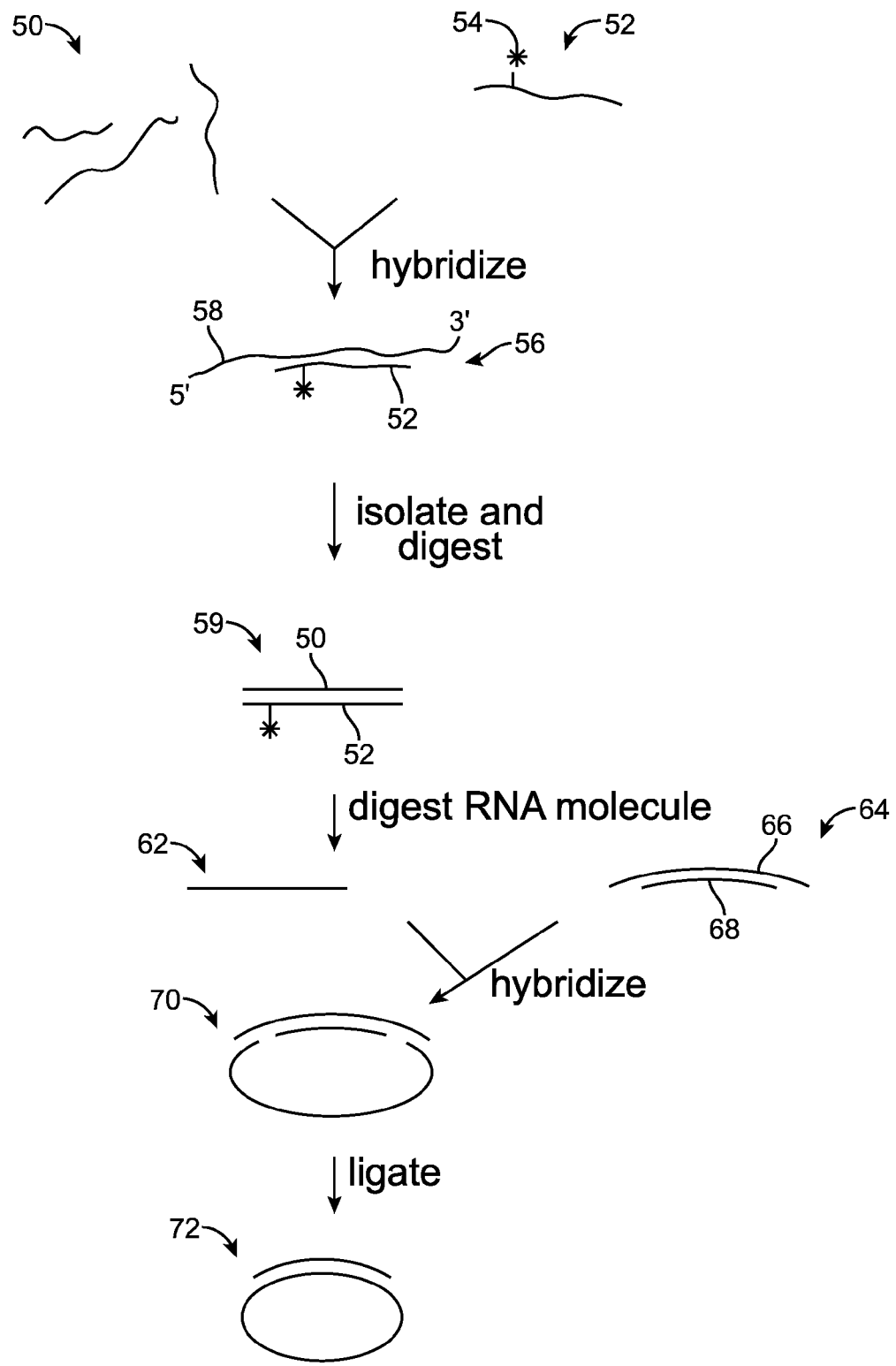
FIG. 3 schematically illustrates another embodiment of the method.

An alternative method of for obtaining a circular product that is similar to the product produced by the method illustrated in FIG. 2 is shown in FIG. 3. In the embodiment shown in FIG. 3, the method uses an RNA oligonucleotide, however any digestible oligonucleotide could be used. With reference to FIG. 3, this embodiment of the method comprises hybridizing randomly sheared genomic DNA 50 to an RNA oligonucleotide 52 comprising a region that hybridizes to a fragment of the randomly sheared genomic DNA to produce an RNA/DNA duplex 56. RNA/DNA duplex 56 comprises a genomic fragment 58 and the RNA oligonucleotide 52, and the genomic fragment contains overhanging sequences. In certain embodiments, RNA oligonucleotide 52 may comprise an optional capture moiety, e.g., a biotin moiety 54. In these embodiments, the method may comprise isolating the enzymatically digested first complex 56 using the capture moiety prior to the digestion step described below. After the duplex is produced, the method comprises enzymatically digesting the overhanging ends of the genomic fragment in the RNA/DNA duplex to provide a duplex 59 comprising a digested genomic fragment 60, which as defined ends. The enzymatically digesting using a method that is similar to that described above. For example, the enzymatically digesting may comprise digesting the first circular complex using a single-strand specific bi-directional exonuclease, exonuclease VII, in the option presence of a polymerase to fill in any ends that have been excessively digested. In other embodiments, the enzymatically digesting may comprises treatment with a cocktail comprising Pfu DNA polymerase and Taq DNA polymerase, a cocktail comprising T4 DNA polymerase and exonuclease VII, treatment with a mung bean nuclease, or treatment with a flap endonuclease in combination with a 3' exonuclease (e.g. exonuclease I, exonuclease T, exonuclease V), or sequential treatment with 5' and 3' exonucleases, for example. The oligonucleotide used in this embodiment may be in the range 10 to 200 nucleotides in length, e.g., 10 to 20, 11 to 30, 31 to 40, 41 to 50, 51-60, 61 to 70, 71 to 80, 80 to 100, 100 to 150 or 150 to 200 nucleotides in length After duplex 59 is produced, the method may comprise digesting the RNA oligonucleotide of the duplex off to release the digested genomic fragment 62. Next, the method may comprise hybridizing the digested genomic fragment 62 with a halo probe 64, examples of which are illustrated in FIG. 1. As shown, a halo probe may comprise a first oligonucleotide 66 that comprises flanking sequences that hybridize to the ends of the digested genomic fragment and a central sequence one or more second oligonucleotides 68 that are complementary to the central sequence of the first oligonucleotide, to provide a second complex 70 in which 5' and 3' ends of the second oligonucleotide are ligatably adjacent to the 3' and 5' ends of the digested genomic fragment. This embodiment of the method comprises ligating the ligatable ends of the digested genomic fragment 70 to the ends of the one or more second oligonucleotides to produce a circular DNA molecule 72. In certain cases (and as shown in FIG. 3) the circular DNA molecule 72 may be covalently circular in that the ends of the digested genomic fragment 60 are ligated to both ends of a single second oligonucleotide. In certain cases the circular DNA molecule 72 may be non-covalently circular if the second embodiment of the halo probe (shown in panel B of FIG. 1) is used. In these embodiments, the first oligonucleotide is hybridized to both the 5' end and the 3' end of the fragmented genomic fragment and holds ends of the fragment together to provide the circular DNA molecule. In this embodiment, the first oligonucleotide holds ends of the circle together. In this embodiment, the 5' end the digested genomic fragment 60 is ligated to the 3' end of one of the second oligonucleotides, and the 3' end the digested genomic fragment 60 is ligated to the 5' and of the other of the second oligonucleotides. In this embodiment, the digestion of the RNA oligonucleotide of duplex 59 may be done using NaOH or RNAseH treatment, although any suitable digestion method may be used.

In any of the above embodiments, the randomly sheared genomic DNA may be produced from genomic DNA using chemical, physical or transposase-catalyzed fragmentation methods, see, e.g., Adey et al (Genome Biology 2010, 11:R119). For example, the physical fragmentation methods may sonication, nebulization, or shearing of genomic DNA. In certain embodiments, prior to performing the method, the genomic DNA may be fragmented to an average size in the range of 100 bp to 10 kb, e.g., 200 bp to 1 kb.

Figure 4:
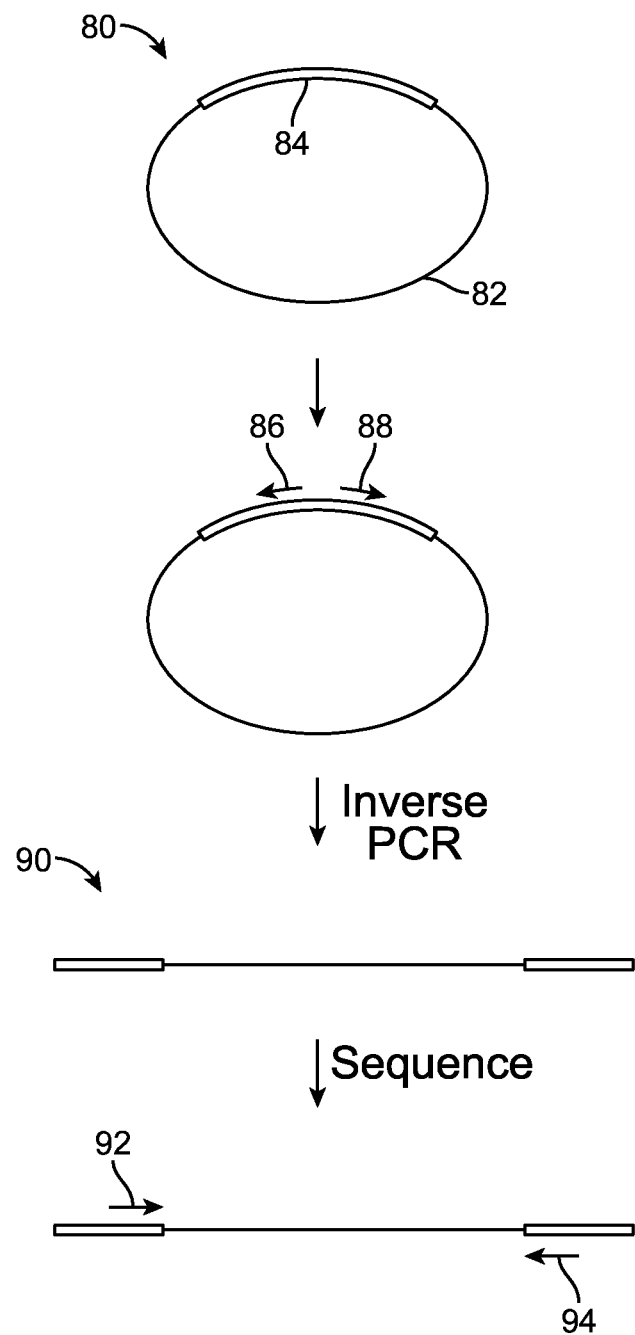
FIG. 4 schematically illustrates one way in which a product DNA molecule can be sequenced.

FIG. 4 schematically illustrates a way in which the digested genomic fragment of any of the above embodiments can be amplified and sequenced. As illustrated in FIG. 4, the product DNA molecule 80 (which comprises the digested genomic fragment 82 and the one or more second oligonucleotides and may be circular, as shown, or linear, depending on which type of halo probe is used), may be amplified using inverse PCR primers 86 and 88 that bind to sites that are provided by the one or more second oligonucleotides. In the embodiment shown, the primers 86 and 88 bind to sites provided by a single second oligonucleotide. In other embodiments, the binding sites for primers 86 and 88 can be provided by the tails of the two second oligonucleotides shown in panel B of FIG. 1. Amplification product 90 may be sequenced to provide the nucleotide sequence of at least part of the digested genomic fragment. In certain cases, the sequencing may be done using primers that hybridize to sequencing primer sites in said one or more second oligonucleotides.

As would be apparent, in certain embodiments, the sequences added by the one or more second oligonucleotides may contain sequences that are compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The sequences may be present in the one or more second oligonucleotides (either in their tails or in the sequence that hybridizes to the first oligonucleotide). In certain cases, the one of more second oligonucleotides may contain two sets of primer binding sites, one for amplifying the circular DNA by inverse PCR, and the other for sequencing the resultant product. The one of more second oligonucleotides may also contain a molecular barcode, positioned downstream of the amplification and sequencing primer binding sites, that can be used to identify from which sample a sequence is derived, or to count how many different starting molecules have been sequenced. In other embodiments, the amplicon may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. Pat Appln Nos. 2006003171 and 20090029477.

The lengths of the various regions of a subject halo probe may vary greatly depending upon the desired application and how much freight (i.e., how many primer binding sites, barcodes, etc.) are carried by the one or more second oligonucleotides. In certain embodiments, the double stranded region of the halo probe may be of 20-100 base pairs (e.g., 30 bp to 60 bp) in length, and the sequences of the flanking regions (which can specifically hybridize to a target fragment in a genome) may be of 10 to 100 bases (e.g., 12-50 bases) in length. As should be readily apparent, the nucleotide sequence of the double stranded region of the halo probe should be designed to that it does not hybridize to the genome under study.

The method described above can be employed to manipulate and analyze DNA from virtually any nucleic acid source, including but not limited to genomic DNA and complementary DNA, plasmid DNA, mitochondrial DNA, synthetic DNA, and BAC clones etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the initial DNA used in the method may be derived from a mammal, where in certain embodiments the mammal is a human.

In certain embodiments, the initial DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed. In addition, the reaction may be multiplex such that a plurality of different target loci (e.g., 10 to 1000) are targeted in a single reaction.

Kits

Also provided by this disclosure are kits for practicing the subject methods, as described above. The subject kits contain at least a halo probe as described, as well as suitable reaction reagents (e.g., buffers etc.) for performing the method. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The invention claimed is:

1. A method comprising:
   (a) hybridizing randomly sheared genomic DNA to a halo probe to produce a first circular complex, wherein said halo probe comprises:
      (i) a first oligonucleotide comprising flanking sequences that hybridize to different regions in a fragment of the randomly sheared genomic DNA and a central sequence: and
      (ii) one or more second oligonucleotides that are complementary to the central sequence of the first oligonucleotide;
   (b) enzymatically digesting the overhanging ends of the genomic fragment in the first circular complex to provide a second circular complex in which 5' and 3' ends of the one or more second oligonucleotide are ligatably adjacent to the 3' and 5' ends of the digested genomic fragment; and
   (c) ligating the ends of the digested genomic fragment of (b) to the ends of the one or more second oligonucleotide to produce a circular DNA molecule.

2. The method of claim 1, wherein said method comprises:
   (d) amplifying the digested genomic fragment from said circular DNA molecule using one or more primers that bind to sites that are provided by the one or more second oligonucleotides.

3. The method of claim 2, further comprising:
   (e) sequencing the amplification product of (d) to provide the nucleotide sequence of at least part of the digested genomic fragment.

4. The method of claim 1, wherein said first oligonucleotide comprises a capture moiety and wherein said method comprises, between steps (a) and (b), isolating said first circular complex using said capture moiety.

5. The method of claim 3, wherein said sequencing is done using prime that hybridize to sequencing primer sites in said one or more second oligonucleotides.

6. The method of claim 1, wherein said enzymatically digesting comprises digesting said first circular complex using a single-strand specific bi-directional exonuclease, in the optional presence of a polymerase.

7. The method of claim 6, wherein said single-strand specific bi-directional exonuclease is exonuclease VII.

8. The method of claim 1, wherein said enzymatically digesting comprises treatment with a Pfu DNA polymerase/Taq DNA polymerase cocktail, or T4 DNA polymerase/exonuclease VII cocktail, treatment with a mung bean nuclease, or treatment with a flap endonuclease in combination with another 3' endonuclease.

9. The method of claim 1, wherein the randomly sheared genomic DNA is produced from genomic DNA using chemical, physical or transposase-catalyzed fragmentation methods.

10. The method of claim 9, wherein said physical fragmentation methods comprise sonication, nebulization, or shearing.

11. The method of claim 1, wherein said one or more second oligonucleotides is a single oligonucleotide that is complementary to the central sequence of the first oligonucleotide.

12. The method of claim 1, wherein said one or more second oligonucleotides is two oligonucleotides, each comprises a first region that hybridizes to said first oligonucleotide, and a second region that provides binding sites for one or more amplification primers.

* * * * *

UNITED STATES PATENT AND TRADEMARK OFFICE
CERTIFICATE OF CORRECTION

PATENT NO. : 10,072,260 B2
APPLICATION NO. : 14/649494
DATED : September 11, 2018
INVENTOR(S) : Scott Robert Happe et al.

Page 1 of 1

It is certified that error appears in the above-identified patent and that said Letters Patent is hereby corrected as shown below:

In the Specification

In Column 1, Line 65, delete "2D" and insert -- 2ND --, therefor.

In Column 2, Line 54, delete "then" and insert -- than --, therefor.

In Column 5, Line 3, delete "42 C" and insert -- 42° C. --, therefor.

In Column 7, Line 14, delete "anenzyme" and insert -- an enzyme --, therefor.

In Column 8, Line 28, delete "digoxgenin;" and insert -- digoxigenin; --, therefor.

In Column 12, Line 49, after "length" insert -- . --.

In Column 15, Line 12, delete "method.The" and insert -- method. The --, therefor.

In the Claims

In Column 15, Line 45, in Claim 1, delete "sequence:" and insert -- sequence; --, therefor.

In Column 16, Line 21, in Claim 5, delete "prime" and insert -- primers --, therefor.

In Column 16, Line 31, in Claim 8, after "cocktail," delete "or".

Signed and Sealed this
Sixth Day of November, 2018

Andrei Iancu
*Director of the United States Patent and Trademark Office*